United States Patent [19]

Baret

[11] 4,393,138
[45] Jul. 12, 1983

[54] METHOD FOR DISINFECTING IMMOBILIZED ENZYMES

[75] Inventor: Jean-Luc A. G. Baret, Moret, France

[73] Assignee: Corning Glass Works, Corning, N.Y.

[21] Appl. No.: 206,099

[22] Filed: Nov. 12, 1980

[30] Foreign Application Priority Data

Dec. 12, 1979 [FR] France ................... 79 30598

[51] Int. Cl.³ .................. C12N 11/14; C12N 11/00; C12N 9/38; C12N 9/92
[52] U.S. Cl. ................................. 435/176; 426/41; 426/330.2; 426/335; 435/174; 435/207; 435/234
[58] Field of Search .............. 426/41, 330.2, 335; 435/174, 176, 177, 180, 207, 234

[56] References Cited

U.S. PATENT DOCUMENTS 4,229,536 10/1980 DeFilippi ........................ 435/176

FOREIGN PATENT DOCUMENTS 2110303 2/1972 France .

OTHER PUBLICATIONS

Pitcher et al., Development of An Adsorbed Lactase Immobilized Enzyme System, Enzyme Engineering, vol. 3, Plenum Publishing Corp., 1978, (pp. 483-496).
Weetall, et al., Preparation of Immobilized Lactase, Biotechnol. and Bioeng., vol. XVI, 1974 (pp. 689-696).

Primary Examiner—David M. Naff
Attorney, Agent, or Firm—W. E. Maycock

[57] ABSTRACT

Disinfecting of immobilized enzymes is carried out by contacting the immobilized enzymes with a dilute aqueous solution of at least one substituted diethylenetriamine at a concentration and for a period of time which is sufficient to substantially kill the contaminating microorganisms without significant deleterious effects on the immobilized enzymes. The substituted diethylenetriamine is preferably dioctyldiethylenetriamine or a mixture of dioctyldiethylenetriamine and trioctyldiethylenetriamine.

4 Claims, No Drawings

METHOD FOR DISINFECTING IMMOBILIZED ENZYMES

BACKGROUND OF THE INVENTION

The present invention relates to a method for disinfecting immobilized enzymes, such as immobilized enzymes used for hydrolyzing lactose to glucose and galactose.

In general, the present invention can be used with any immobilized enzyme as long as the immobilized enzyme is not adversely affected by the disinfecting agent. For simplicity, however, the discussion which follows is limited to immobilized enzymes employed in the hydrolytic conversion of lactose to glucose and galactose, but is not to be construed as in any way limiting the spirit and scope of the invention.

In 1976, French cheese production reached approximately one million tons, resulting in the production of more than six million tons of whey as a by-product. Such whey contains, per liter, approximately 6 to 9 g. of protein, 45 to 50 g. of lactose, 6 to 8 g. of mineral salts, and 1 to 2 g. of fat. World-wide, the amount of lactose available from whey alone in 1977 totaled almost 3.5 million tons.

In the past, whey was regarded as a waste product and was discharged into sewers or streams and rivers. Because of increasing concerns over environmental pollution, much of the whey is being processed into a variety of animal and human foods. For example, the development of high performance ultrafilters now permits the separation of whey protein from the whey. Such protein is of exceptional value. For example, a 35 percent concentrate of whey protein can replace nonfat dry milk in many food products, such as baked goods, beverages, and frozen desserts. Unfortunately, the separation of proteins from whey results in a liquid fraction, called permeate, which until recently has had little or no value.

With the advent of immobilized enzymes, however, hydrolysis of the lactose in the permeate, either with or without demineralization, has become commercially feasible. Because of the presence of glucose and galactose, hydrolyzed lactose is much sweeter and more soluble than lactose alone. Thus, the hydrolyzed product is a functional sweetener which can be used in the preparation of pastries, milk-based desserts, and frozen confections such as ice cream. Furthermore, the hydrolyzed product is an efficiently fermentable mixture suitable for use as a fermentation substrate in, for example, the brewing and pharmaceutical industries.

It also is possible to carry out the hydrolysis of the lactose in whey without a prior ultrafiltration step and either with or without demineralization. The product, which still contains proteins, is similar to hydrolyzed permeate and, consequently, it also can be used in the food industry as already described.

Various methods for hydrolyzing lactose are, of course, well known to those having ordinary skill in the art. Enzymatic hydrolysis is especially useful for the production of food-related products and, as already indicated, the use of immobilized enzymes is particularly attractive.

By way of illustration only, H. H. Weetall et al., *Biotechnol. Bioeng.*, 16, 295 (1974), discuss the preparation of immobilized lactase and its use in the enzymatic hydrolysis of acid whey. The enzyme, isolated from both fungi and yeast, was immobilized on zirconia-coated porous glass particles. The substrate consisted of either aqueous lactose solution or acid whey permeate.

Additionally, L. E. Wierzbicki et al., *Biotechnol. Bioeng.* 16, 397 (1974), reported on the hydrolysis of lactose in acid whey using lactase ($\beta$-galactosidase) immobilized on porous glass particles with emphasis on the preparation and characterization of a reusable catalyst for the production of low-lactose dairy products. Partially purified lactases from *Aspergillus niger, Lactobacillus helveticus,* and *Saccharomyces lactis* were immobilized on porous glass particles. The substrate consisted of acid whey powder which had been reconstituted in water to the appropriate solids concentration. In some instances, the reconstituted acid whey was deproteinized by heating in a boiling water bath for five minutes.

Finally, H. H. Weetall et al., *Biotechnol. Bioeng.*, 16, 689 (1974), describe the preparation of immobilized lactase as part of continued studies on the enzymatic hydrolysis of lactose. A fungal lactase was employed, immobilized on zirconia-coated controlled-pore glass and porous titania particles. The resulting immobilized enzyme preparations were used for the hydrolysis of lactose in whole sweet whey, whole acid whey, acid whey ultrafiltrate, and pure lactose.

As noted by H. H. Weetall et al., *Biotechnol. Bioeng.*, 16, 689 (1974), bacterial contamination of the whey substrate was a major problem. The continued growth of microorganisms clogged the columns. The use of 2 percent gluteraldehyde at pH 4.0 was found to kill the bacteria without destroying the activity of the immobilized enzyme. These authors stated that a sanitizing procedure would be absolutely necessary in any plant situation.

It is apparent, however, that any commercially-viable sanitizing or disinfecting procedure must effectively destroy substantially all of the contaminating microorganisms without any appreciable harmful effect on the immobilized enzymes. Furthermore, in cases where the product is intended for use in the food industry, the disinfecting agent often must meet governmental regulatory requirements.

Until now, no truly satisfactory disinfectant has been available. Acetic acid, which is commonly used as a dilute aqueous solution, gives only fair results. Moreover, other known disinfectants, such as halogen derivatives, organic acids, quaternary ammonium compounds, biguanidine polymers, and the like tend to be unsuitable because of partial or complete inactivation of the enzymes.

Thus, there still is a need for a commercially-viable sanitizing or disinfecting procedure for immobilized enzymes which is effective without significant deleterious effects on the immobilized enzymes.

SUMMARY OF THE INVENTION

It therefore is an object of the present invention to provide a method for disinfecting immobilized enzymes.

Another object of the present invention is to provide a method for disinfecting immobilized enzymes which effectively destroys substantially all of the contaminating microorganisms without significant deleterious effects on the immobilized enzymes.

These and other objects will be apparent to those skilled in the art from a consideration of the specification and claims which follow.

Accordingly, the present invention provides a method for disinfecting immobilized enzymes which comprises contacting the immobilized enzymes with a dilute aqueous solution of at least one substituted diethylenetriamine at a concentration and for a period of time which is sufficient to substantially kill the contaminating microorganisms without significant deleterious effects on the immobilized enzymes, which diethylenetriamine has the following general formula:

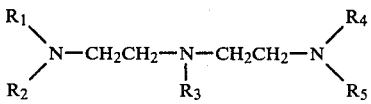

in which $R_1$, $R_2$, $R_3$, $R_4$, and $R_5$ are monovalent groups (1) independently selected from the group consisting of hydrogen and octyl, with the proviso that at least two of $R_1$, $R_2$, $R_3$, $R_4$, and $R_5$ must be octyl, or (2) in which $R_1$ and $R_4$ are hydrogen and $R_2$, $R_3$, and $R_5$ independently are selected from the group consisting of hydrogen, benzyl, and lauryl, with the proviso that no two of $R_2$, $R_3$, and $R_5$ can be the same.

DETAILED DESCRIPTION OF THE INVENTION

As is well known in the art, lactose is at least about 80 percent hydrolyzed into glucose and galactose by passing a lactose-containing aqueous solution through a column containing immobilized lactase, typically at a temperature below about 60° C. The effluent can be partially concentrated to yield a syrup suitable for use as a sweetener in various foods.

The lactase employed in such a process is produced by a variety of microorganisms, such as fungi, bacteria, and yeasts. Fungal lactases perhaps are the most common, e.g., lactases isolated from *Aspergillus niger* and *Aspergillus oryzae*. Techniques for isolating lactases from microorganisms are, of course, well known in the art.

Immobilization of the enzyme is readily accomplished by various methods which also are known. For a recent review of immobilization techniques, see I. Chibata, Editor, "Immobilized Enzymes", Halsted Press, John Wiley & Sons, Inc., New York, 1978, pp. 1-73. Although the method of immobilization is not known to be critical, the method of the present invention is especially well-suited for use with enzymes bound to water-insoluble supports or carriers. If desired, such supports can be porous, thereby allowing an increased enzyme loading per unit mass of support. In general, enzymes are bound to water-insoluble supports by physical adsorption, ionic binding, covalent binding, or some combination thereof.

The water-insoluble supports generally can be either organic or inorganic. Examples of organic supports include, among others, polyesters, such as poly(ethylene terephthalate); polyamides, such as nylon 6 and nylon 6.6; polyacrylates; polymethacrylates; polyacrylamides; poly(acrylic acid); poly(methacrylic acid); poly(galacturonic acid); poly(aspartic acid); ethylene-maleic anhydride copolymers; polyolefins, such as polyethylene, polypropylene, polybutene, and polybutadiene; polystyrene; poly(aminostyrene); poly(vinyl chloride); poly(vinyl alcohol); poly(vinylidene chloride); cellulose and derivatives thereof; agarose gels; dextran gels and derivatives thereof; polysaccharides; polypeptides; collagen; and the like.

The inorganic supports can be classified as siliceous or nonsiliceous metal oxides. Examples of siliceous supports include, among others, glass, silica, wollastonite, bentonite, cordierite, and the like. Examples of nonsiliceous metal oxides include, among others, alumina, spinel, apatite, nickel oxide, titania, zirconia, and the like.

In general, the water-insoluble support can be in any desired shape or form. The support can be particulate in nature, varying from a finely-divided powder to a coarse granular material, or the support can be a continuous, shaped article such as a flat or curved sheet or pellet, or a three-dimensional article such as a rectangular or cylindrical tube or complex monolith. As a practical matter, however, the support most often will be particulate.

For examples of procedures for immobilizing enzymes on inorganic supports, by way of illustration only, see U.S. Pat. No. 3,519,538 (which corresponds with French Pat. No. 2,020,527), U.S. Pat. No. 3,556,945 (which corresponds with French Pat. No. 2,001,336), and U.S. Pat. Nos. 3,666,627 and 3,802,997 (which correspond with French Pat. No. 2,020,661).

As already indicated, the substituted diethylenetriamines which are useful in the method of the present invention have the following general formula:

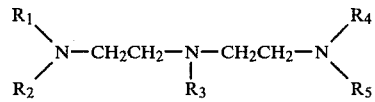

in which $R_1$, $R_2$, $R_3$, $R_4$, and $R_5$ are monovalent groups (1) independently selected from the group consisting of hydrogen and octyl, with the proviso that at least two of $R_1$, $R_2$, $R_3$, $R_4$, and $R_5$ must be octyl, or (2) in which $R_1$ and $R_4$ are hydrogen and $R_2$, $R_3$, and $R_5$ independently are selected from the group consisting of hydrogen, benzyl, and lauryl, with the proviso that no two of $R_2$, $R_3$, and $R_5$ can be the same.

Such substituted diethylenetriamines and methods of preparing them are described in French Pat. Nos. 2,080,797 (or equivalent Canadian Pat. No. 910,192 and U.S. Pat. No. 3,912,816) and 2,110,303 (or equivalent Canadian Pat. No. 960,963) and in German Pat. No. 2,115,549. Such compounds possess biocidic properties. Preferably, the synergistic mixture of dioctyldiethylenetriamine and trioctyldiethylenetriamine described in French Pat. No. 2,110,303, supra, commercially available from Th. Goldschmidt AG, West Germany, under the name "Tego Diocto BS", will be employed in the method of the present invention.

Such substituted diethylenetriamines are employed in dilute aqueous solutions, typically at a concentration of from about 0.1 to about 0.5 percent by weight, although lower or higher concentrations can be used. In general, the concentration of substituted diethylenetriamine, the total volume of aqueous solution, and the duration of the disinfecting treatment can vary widely, depending, at least in part, on the substituted diethylenetriamine(s) employed, the severity of the microbial contamination, the type(s) of microorganism(s) present, and the amount of immobilized enzyme. Nevertheless, such treatment conditions or parameters are readily determined by those having ordinary skill in the art. Most frequently, however, treatment for about 15–30 minutes with 5 to 10 liters of a 0.1 percent by weight disinfecting solution of, for example, Tego Dioctyl BS, per kilogram of immobilized enzyme has proven satisfactory.

In one embodiment of the present invention, the immobilized enzyme is simply placed in a bath of disinfecting solution. Optionally, the bath can be shaken, stirred, circulated by a pumping means, or otherwise agitated.

In another embodiment, the disinfecting solution is circulated through the column or reactor containing the immobilized enzyme. Preferably, such circulation of disinfecting solution is carried out in a reverse flow mode, i.e., in the direction opposite to the flow of feed solution through the column or reactor. Where the enzyme has been immobilized on a particulate support and the column or reactor design so allows, the rate of the reverse flow of disinfecting solution desirably is such that the immobilized enzyme particles are fluidized. Such fluidization prevents channeling and ensures complete contact of the immobilized enzyme with disinfecting solution.

It should be noted that any disinfecting solution can be used several times in order to reduce the cost of the disinfecting operation. When the disinfecting solution is recycled, however, some additional treatments may be either desirable or necessary, such as, for example, filtering to remove cell debris and adjustments in pH.

In yet another embodiment of the present invention, the substituted diethylenetriamine(s) can be incorporated in the feed solution to be processed by the immobilized enzyme. By this means, microbial contamination of the immobilized enzyme can be minimized or even prevented. Of course, such preventative treatment can be used alone or in conjunction with a disinfecting procedure already described.

The present invention is further described, but not limited, by the following examples which illustrate comparative tests and certain preferred embodiments.

EXAMPLE 1

Disinfection of a Reactor Charged with Immobilized Lactase Derived from A. Niger and Used for the Hydrolysis of Whey Permeate After thorough rinsing with water to eliminate as much organic material as possible, a column charged with 45 kg. of immobilized A. niger-derived lactase prepared by bonding the enzyme to a particulate silica support by the procedure described in U.S. Pat. No. 3,519,538 was treated for about 20 minutes by passing through the column in a reverse flow mode an aqueous 0.1 percent by weight solution of Tego Diocto BS at a rate of 1,000 liters per hour. The column then was rinsed with water.

The microorganism counts in the wash water before and afrer the disinfecting treatment were as follows (Table I).

TABLE I

| Wash Water Microorganism Counts | | | |
|---|---|---|---|
| | Before | After | Treatment Efficiency[a] |
| Total Microorganisms | 470,000 | 6,000 | 98.7% |
| Yeasts and Molds | 1,550 | 65 | 95.8% |

[a][(Before − After)/Before] × 100

The above counts clearly show the germicidal action of the disinfectant used.

EXAMPLES 2 AND 3

Comparative Tests

Disinfection of a Reactor Charged with Immobilized Lactase Derived from A. niger and Used for the Hydrolysis of Whey Permeate in a Routine Treatment for Contamination Two tests were carried out involving the operation, under industrial conditions, of the immobilized enzyme reactor or column of Example 1. The feed solution consisted of whey permeate at pH 3.5, the lactose contained therein being hydrolyzed to glucose and galactose. The column or reactor temperature was maintained at 38° C. During the tests, the contamination of the effluent and activity of the immobilized lactase were measured daily.

In the first test, Example 2, the reactor was decontaminated with Tego Diocto BS as described in Example 1. The reactor then was treated daily for 30 minutes with 500 liters of a 0.1 percent by weight aqueous solution of acetic acid which was passed through the reactor at a rate of 1,000 liters per hour.

In the second test, Example 3, carried out after the first test, the reactor was decontaminated again with Tego Diocto BS as described in Example 1. The reactor then was treated daily with Tego Diocto BS under the same conditions as the initial decontamination, except that no preliminary rinsing was performed.

The contamination of the effluent, expressed as microorganism counts per ml., is summarized in Table II and the immobilized lactase activity, expressed as International Units per g. of immobilized enzyme, is summarized in Table III.

TABLE II

| Summary of Effluent Contamination | | |
|---|---|---|
| Day | Total Microorganisms/ml. | Yeasts/ml. |
| | Example 2 | |
| 1 | First disinfection of the reactor | |
| 2 | 180,000 | 150,000 |
| 3 | 980,000 | 780,000 |
| 4 | 1,200,000 | 800,000 |
| 5 | 1,390,000[a] | 940,000 |
| | Example 3 | |
| 6 | Second disinfection of the reactor | |
| 7 | 510 | 200 |
| 8 | 1,500 | 800 |
| 9 | 3,300 | 1,100 |
| 10 | 5,800 | 1,100 |
| 11 and following | Continuation of operations[b] | |

[a]Test stopped because of excessive contamination
[b]Subsequent operations confirmed the reduction of microbial contamination as a result of the method of the present invention.

TABLE III

| Summary of Immobilized Lactase Activity | | |
|---|---|---|
| Day | Activity, I.U./g. | Average Activity, I.U./g. |
| | Example 2 | |
| 1 | First disinfection of the reactor | |
| 2 | 159 | |
| 3 | 184 | |
| 4 | 165 | |
| 5 | 168 | 169 |
| | Example 3 | |
| 6 | Second disinfection of the reactor | |
| 7 | 161[a] | |
| 8 | 189 | |
| 9 | 176 | |
| 10 | 188 | |
| 11 | 204 | |

TABLE III-continued

| Summary of Immobilized Lactase Activity | | |
|---|---|---|
| Day | Activity, I.U./g. | Average Activity, I.U./g. |
| 12 | 198 | 186 |

[a] The activity was distorted by flow rate problems

Examples 2 and 3 clearly show that the method of the present invention ensures a much more effective control (by a factor of at least $10^3$) of the microbial contamination than does the use of acetic acid. At the same time, the method of the present invention is much less harmful to the immobilized enzyme. In fact, Tego Diocto BS, at concentrations of from about 0.1 to about 0.5 percent by weight, does not affect the enzymatic activity of soluble *A. niger*-derived lactase, i.e., enzyme which has not been immobilized.

Thus, Examples 2 and 3 clearly demonstrate that the method of the present invention constitutes a disinfecting treatment of choice for immobilized enzyme reactors.

EXAMPLE 4

Investigation of the Effect of the Method of the Present Invention on Immobilized *A. oryzae*-derived Lactase Used for Hydrolyzing Lactose A. Variations of Enzymatic Activity with Time The variations of the enzymatic activity of immobilized *A. oryzae*-derived lactase were determined under laboratory conditions for each of three different cases: (1) use of the immobilized lactase to hydrolyze a lactose solution at a pH of 4.2 and a temperature of 35° C. (reference test); (2) use of the immobilized lactase, after disinfection in the fluidized state for 30 minutes with a 0.1 percent by weight solution of Tego Diocto BS, for hydrolyzing the lactose solution employed in the reference test; and (3) use of the immobilized lactase of the reference test for hydrolyzing a lactose solution at pH 4.5 and at a temperature of 35° C., which solution also contains 0.1 percent by weight of Tego Diocto BS. The results obtained are summarized in Table IV.

TABLE IV

| Summary of Variations of Enzymatic Activity with Time | | | |
|---|---|---|---|
| Time, | Enzymatic Activity, I.U./g. | | |
| Hours | Case 1 | Case 2 | Case 3 |
| 2 | 114 | 114 | 125 |
| 3 | 120 | 114 | 125 |
| 4 | 129 | 119 | 134 |
| 5 | 124 | 117 | 132 |
| Average | 121 | 116 | 129 |

The above results show that the enzymatic activity of the immobilized lactase is essentially unaffected by contact with the disinfecting solution and that hydrolysis of lactose proceeds normally, even in the presence of the disinfectant.

B. Comparison of the Effects of Repeated Treatments

The tests were carried out over a five-day period. Each day the charge of immobilized *A. oryzae*-derived lactase was used for 16 hours to hydrolyze a lactose solution at a pH of 4 and a temperature of 35° C. The immobilized enzyme charge then was treated for 30 minutes under fluidizing conditions with either a 1 percent by weight acetic acid solution (reference test) or a 0.1 percent by weight solution of Tego Diocto BS (test according to the present invention). The results are given in Table V.

TABLE V

| Summary of the Effects of Repeated Treatments on Enzymatic Activity | | |
|---|---|---|
| | Enzymatic Activity, I.U./g. | |
| Time, Days | Reference Test | Test According to Present Invention |
| 1 | 143 | 135 |
| 2 | 144 | 151 |
| 3 | 139 | 127 |
| 4 | 155 | 144 |
| 5 | 126 | 124 |

The above results indicate that there is no significant difference in enzymatic activity resulting from the two treatments.

The use of the method of the present invention as a routine treatment for immobilized *A. oryzae*-derived lactase, however, can be recommended. As shown earlier, the disinfectants employed in the method of the present invention are far more effective germicides than acetic acid. Furthermore, the method of the present invention clearly has no deleterious effects on immobilized *A. oryzae*-derived lactase.

Although the present invention primarily has been described in relation to the disinfection of immobilized lactase, it is to be understood that the method of the present invention can be applied to other immobilized enzymes. By way of illustration only, certain immobilized enzyme systems are being used in the food and pharmaceutical industries and include, among others, immobilized glucoamylase, glucose isomerase, and penicillin acylase.

Example 5 below illustrates the application of the method of the present invention for disinfecting an immobilized glucose isomerase which is used to convert glucose to fructose.

EXAMPLE 5

Effect of the Method of the Present Invention on an Immobilized Glucose Isomerase Glucose isomerase was immobilized on an alumina support by the procedure described in U.S. Pat. No. 3,868,304 (which corresponds with French Pat. No. 2,218,385). This enzyme is sensitive to variations in the osmotic pressure of the aqueous medium in which it is present. The enzyme is used industrially to obtain fructose from glucose solutions containing about 45-50 percent total solids and with a pH of about 8.4 and a temperature of about 60° C.

In laboratory experiments simulating industrial conditions, the following parameters were studied:

A. The loss of enzymatic activity associated with a water rinse at pH 8.4 and a temperature of 60° C.

B. The loss of enzymatic activity associated with the treatment at the same pH and temperature by a 0.1 percent by weight aqueous solution of Tego Diocto BS.

The enzymatic activity was determined each day on the basis of 16 hours of continuous fructose production. The data obtained are summarized in Table VI.

TABLE VI

| Effect of Water and Disinfectant Solution on the Enzymatic Activity of Immobilized Glucose Isomerase | | | | |
|---|---|---|---|---|
| Parameter | Day | Reactor Output, cm³/hr. | % Conversion[a] | Activity, I.U./g. |
| A | 1 | 73 | 39 | 169 |

TABLE VI-continued

Effect of Water and Disinfectant Solution on the
Enzymatic Activity of Immobilized Glucose Isomerase

| Parameter | Day | Reactor Output, cm³/hr. | % Conversion[a] | Activity, I.U./g. |
|---|---|---|---|---|
| | | Water rinse for 90 minutes | | |
| | 2 | 72.6 | 32 | 116 |
| B | 1 | 77 | 40 | 189 |
| | | Disinfectant treatment for 90 minutes | | |
| | 2 | 77 | 33 | 128 |

[a] Percent of glucose in the feed solution converted to fructose

In both cases, a loss of enzymatic activity of about 30 percent was obtained. This loss was caused by the desorption and elution of the enzyme from the alumina support when the immobilized enzyme was exposed to a more dilute solution having a significantly higher osmotic pressure. Thus, no observable decrease in enzymatic activity can be attributed to the treatment of the immobilized enzyme with disinfectant.

It is to be understood that the foregoing detailed description is given merely by way of illustration and that many variations may be made therein without departing from the spirit and scope of the invention. For example, the term "immobilized enzymes" as used herein is meant to include a single enzyme immobilized on a suitable support and a single type of enzyme isolated from two or more sources or two or more types of enzymes similarly immobilized. In the latter case, the several enzymes can be immobilized on the same support or different supports which then are comingled for use. Other variations will be apparent to those having ordinary skill in the art.

What is claimed is:

1. A method for disinfecting immobilized enzymes which comprises contacting the immobilized enzymes with a dilute aqueous solution of at least one substituted diethylenetriamine at a concentration and for a period of time which is sufficient to substantially kill the contaminating microorganisms without significant deleterious effects on the immobilized enzymes, in which the enzymes are selected from the group consisting of lactase and glucose isomerase, the enzymes are immobilized on an inorganic support, and the substituted diethylenetriamine is selected from the group consisting of dioctyldiethylenetriamine and a mixture of dioctyldiethylenetriamine and trioctyldiethylenetriamine.

2. The method of claim 1 in which the enzymes are immobilized on a particulate support.

3. The method of claim 2 in which the immobilized enzymes are contained in a reactor having a columnar configuration and the dilute aqueous solution is passed through the column in a reverse flow mode under conditions sufficient to fluidize the particulate immobilized enzyme.

4. The method of claim 1 in which one or more of the substituted diethylenetriamines are incorporated in the feed solution.

* * * * *